United States Patent [19]

Delp

[11] 4,306,320
[45] Dec. 22, 1981

[54] PROSTHETIC FOOT

[76] Inventor: Larry D. Delp, 210 Timberlane, Collensville, Conn. 06022

[21] Appl. No.: 148,539

[22] Filed: May 9, 1980

[51] Int. Cl.³ ............................................. A61F 1/08
[52] U.S. Cl. ............................................. 3/6.1; 3/31; 3/7
[58] Field of Search ..................... 3/6, 6.1, 7, 8, 31

[56] References Cited

U.S. PATENT DOCUMENTS

| | | | |
|---|---|---|---|
| 832,270 | 10/1906 | McGrady | 3/13 |
| 835,428 | 11/1906 | Hogan | 3/6.1 X |
| 1,343,298 | 6/1920 | Worman | 3/16 |
| 1,581,815 | 4/1926 | Scully | 3/6.1 |
| 3,551,914 | 1/1971 | Woodall | 3/6 |
| 3,754,286 | 8/1973 | Ryan | 3/7 X |
| 3,920,610 | 11/1975 | Wagner | 3/6.1 X |

FOREIGN PATENT DOCUMENTS

| | | | |
|---|---|---|---|
| 528796 | 8/1921 | France | 3/7 |
| 328441 | 8/1935 | Italy | 3/6 |
| 628958 | 9/1949 | United Kingdom | 3/6 |

Primary Examiner—Clifford D. Crowder
Attorney, Agent, or Firm—Huebner & Worrel

[57] ABSTRACT

A prosthetic foot which has an ankle member adapted for mounting on the leg of a user and provided with a forwardly disposed wedging surface; a toe member provided with a wedging surface facing the wedging surface of the ankle member; a resilient sheet extended longitudinally of the foot beneath the members, connecting them for relative pivotal movement as the sheet flexes; a wedge disposed between the surfaces; and a screw mounted on the sheet and engaging the wedge so that rotation of the screw adjustably positions the wedge between the surfaces pivoting the members selectively to arch and to flatten the interconnected members to adapt the foot for use with shoes having heels of different heights.

7 Claims, 9 Drawing Figures

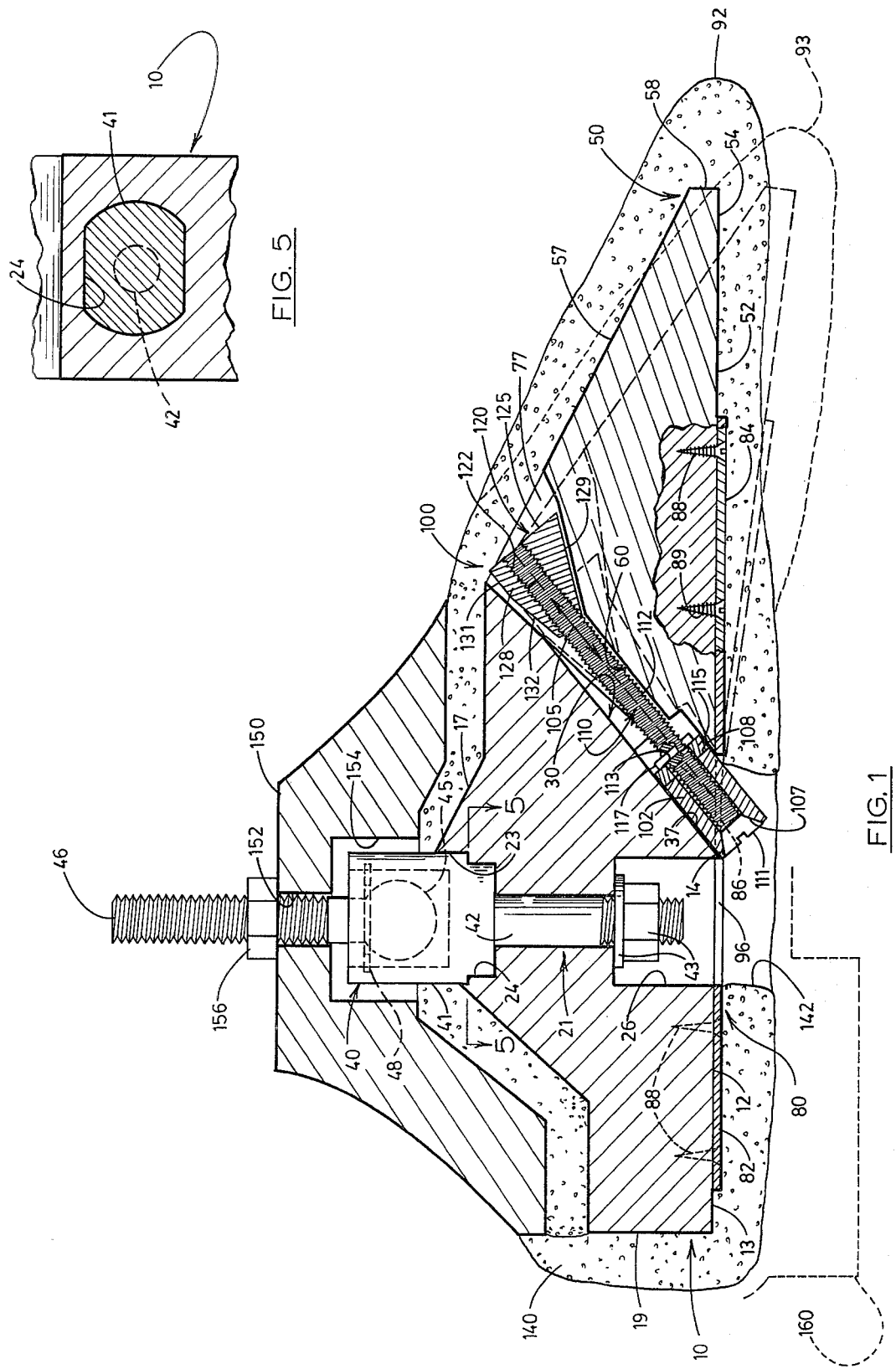

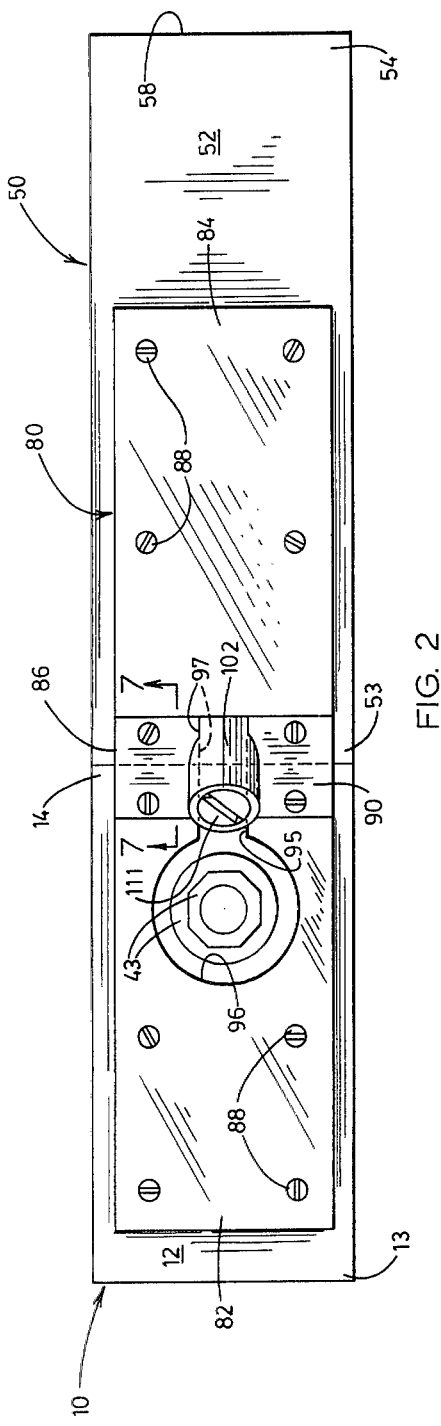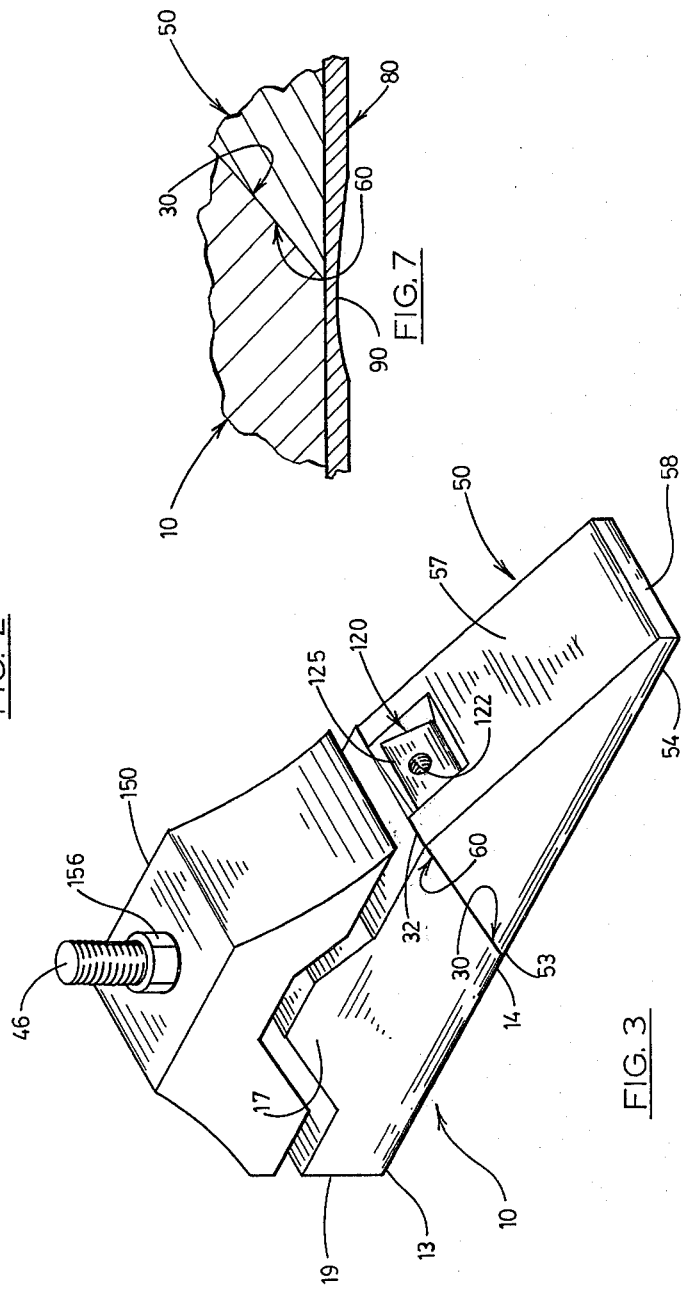

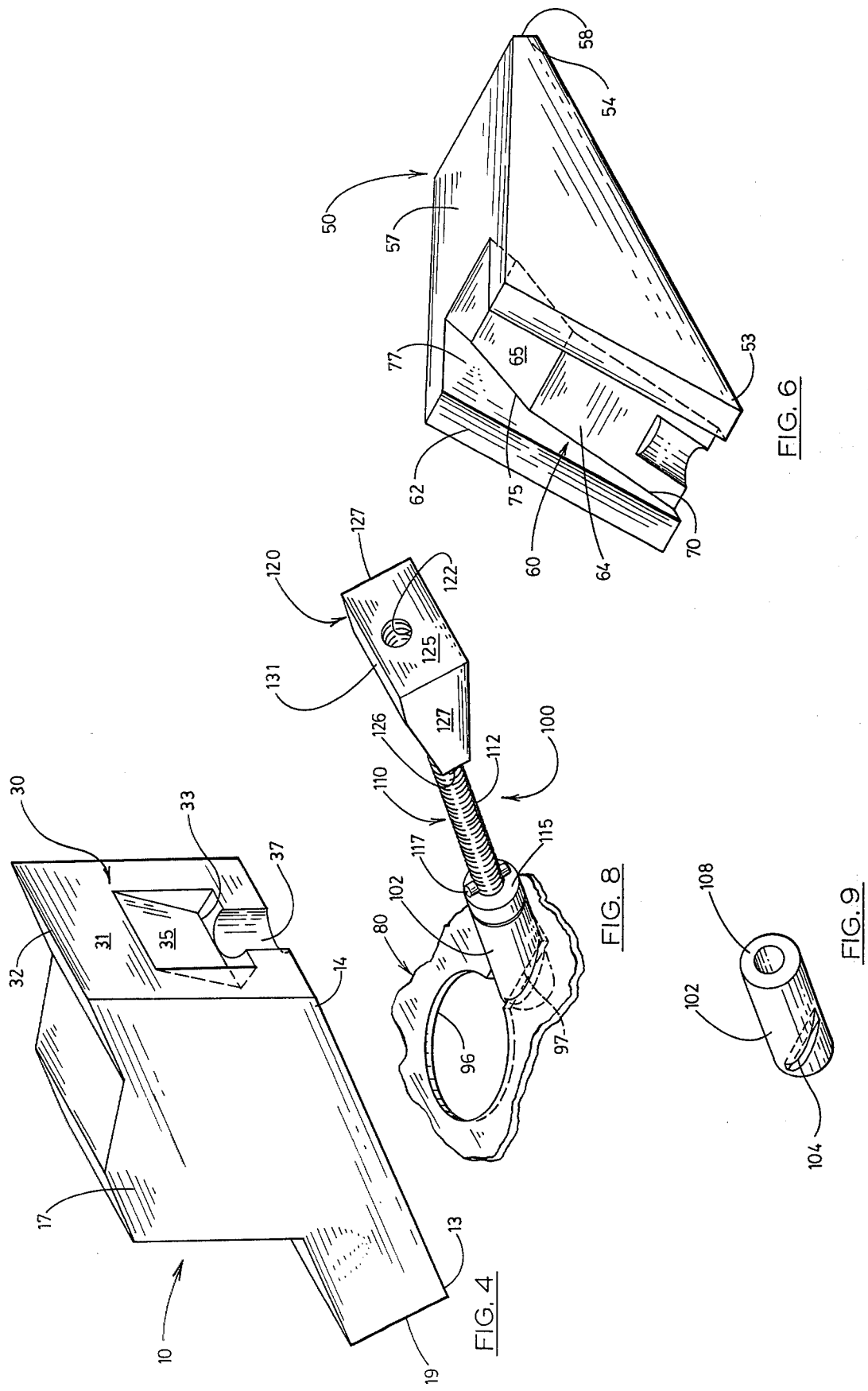

PROSTHETIC FOOT

BACKGROUND OF THE INVENTION

1. Field of the Invention

The present invention relates to a prosthetic foot and more particularly to a prosthetic foot adjustable for use with shoes having heels of different heights.

2. Description of the Prior Art

The prior art includes prosthetic foot structures of a variety of types. One well-known type has a ball and socket ankle joint while another well-known type has a solid ankle. Both of these types utilize a cushioned heel and a flexible toe to simulate the action of a natural foot in walking.

An individual foot of these and all other prior art structures is proportioned and dimensioned for use only with a shoe heel of a predetermined height unlike natural feet which can, of course, adjust to heels of different heights. However, prior art prosthetic feet, lacking the elaborate and flexible structure of natural feet, cannot accommodate shoe heels varying substantially from the predetermined height to which they are individually adapted. When used with a different height of heel, prosthetic feet cause discomfort, require increased exertion by the user, and result in a clumsy and uneven gait.

Since each prosthetic foot is individually fitted to a prosthetic leg, it is necessary to provide a prosthetic leg and prosthetic foot for every height of shoe heel which will be worn by the user of such a device. This is inconvenient at best and is prohibitively expensive for most users of a prosthetic foot.

It has, therefore, long been recognized that it would be highly advantageous to provide a prosthetic foot which is adapted for use with shoe heels of varying heights and yet is relatively lightweight and sturdy.

PRIOR ART STATEMENT

Characterizing the closest prior art of which the applicant is aware, attention is invited to the following U.S. Pat. Nos.:

McGrady: 832,270; Oct. 2, 1906
Worman: 1,343,298; June 15, 1920
Woodall: 3,551,914; Jan. 5, 1971
Ryan: 3,754,286; Aug. 28, 1973
Wagner: 3,920,610; Nov. 18, 1975

The McGrady Pat. No. 832,270 is believed relevant in its disclosure of an artificial foot having a pivotally mounted toe section. The pivotal movement of the toe section is apparently not controlled.

The Worman Pat. No. 1,343,298 is believed relevant in its disclosure of an artificial foot in which the bending of the ankle joint is controlled by a spring whose force is adjusted by a screw-threaded bolt and in which the toe portion of the foot is mounted by a hinge and has its pivotal movement controlled by a spring. The arch of the foot is not adjustable.

The Woodall Pat. No. 3,551,914 is believed relevant in its disclosure of a toe section mounted by a flexible strip. This section is pivoted upwardly by a spring when weight is taken off the foot to give the section a natural movement. No adjustment is provided to vary the "degree of arch" or other shape of the foot.

The Ryan Pat. No. 3,754,286 is believed relevant in its disclosure of an artificial foot having a sole plate. This sole plate is evidently not intended to flex substantially since it is "of relatively heavy steel," and no adjustments are provided for the form of the foot.

The Wagner Pat. No. 3,920,610 discloses the use of flexible strips, preferably of nylon, to provide a desired resiliency of the toe of an artificial foot. However, no adjustment is provided for the form of the foot or the resiliency of the strips once the foot is assembled.

SUMMARY OF THE INVENTION

It is an object of the present invention to provide an improved prosthetic foot.

Another object is to provide such a prosthetic foot which is selectively adjustable for use with shoe heels of different heights.

Another object is to provide a prosthetic foot which is readily adjustable by the user when it is desired to wear shoes having different heel heights.

Another object is to provide a prosthetic foot which possesses the foregoing advantages and is adaptable for use with advantageous prior art prosthetic foot structures.

Another object is to provide such a prosthetic foot which is relatively light in weight, sturdy, and economical, and achieves the above and other objects and advantages through the use of a structure characterized by a toe member pivotally connected to an ankle member to vary the degree to which the foot is arched.

BRIEF DESCRIPTION OF THE DRAWINGS

FIG. 1 is a vertical section of a prosthetic foot embodying the principles of the present invention and including a layer of resilient material. Alternate positions of certain elements and a fragmentarily represented shoe heel are depicted in dash lines.

FIG. 2 is a bottom plane view of the foot of FIG. 1 without the resilient material.

FIG. 3 is a perspective view at a reduced scale of the foot without the resilient material.

FIG. 4 is a perspective view of a rear keel utilized in the foot. The keel is depicted in a position which is rotated approximately 45° counter-clockwise from its position in FIG. 1.

FIG. 5 is a fragmentary section of the rear keel and of a ball joint assembly utilized in the foot.

FIG. 6 is a perspective view of a forward keel utilized in the foot.

FIG. 7 is a fragmentary section of the keels and a hinge plate taken on line 7—7 of FIG. 2.

FIG. 8 is a perspective view of a wedge assembly used in the foot. The assembly is depicted in a position rotated approximately 45° counter-clockwise from its position in FIG. 1.

FIG. 9 is a perspective view of a collar utilized in the wedge assembly.

DESCRIPTION OF THE PREFERRED EMBODIMENT

Referring with greater particularity to the drawings, FIGS. 1, 2, and 3 depict a prosthetic foot which embodies the principles of the present invention.

The foot includes an ankle member or rear keel 10, best shown in FIGS. 1 through 5, and typically unitarily constructed from a block of strong but lightweight wood. This member has a downwardly disposed, substantially horizontal, planar sole surface 12 which is generally rectangular and is elongated longitudinally of the foot, having a heel end 13 and an opposite forward end 14. The upper portion of the keel is provided with a central hump 17 and the keel has a heel portion 19 extending above the sole surface from the hump to the heel end of this surface. A generally circular opening 21 extends vertically through the keel from the top of the hump to the sole surface. An upper counter bore 23 forms the upper end portion of this opening. The lower end of the counter bore is terminated downwardly by a recess 24 which has a pair of parallel opposite sides. A lower counter bore 26 forms the lower end portion of the opening. The portion of the opening between the recess and the lower counter bore is a bore which is substantially smaller in diameter than the counter bores. The heretofore described features of the keel can have any shapes and dimensions appropriate to the prosthetic art.

The keel 10 has a forward end or side 30 which includes a peripheral planar surface 31, best shown in FIGS. 1 and 4, extending upwardly and forwardly from the forward end 14 of the sole surface 12 to a upper edge 32 of the peripheral surface. The peripheral surface is disposed at a lesser included angle of approximately 50° to the plane of the sole surface. The forward side has a groove 33 which is transversely centered in it. The width of the groove is approximately one-half of the width of the forward side. The bottom of the groove is a planar, transversely extending, forwardly and downwardly facing wedging surface 35 which is disposed at an angle of approximately 40° to the plane of the sole surface. As best shown in FIG. 1, this wedging surface intersects the peripheral surface toward the upper edge of the forward side. The groove is intersected by a slot 37 which extends from the groove to the sole surface. The slot is substantially narrower than the groove and the bottom of the slot is a downward and rearward coplanar extension of the wedging surface.

The rear keel 10, typically, is provided with a ball joint assembly 40 which is received in the opening 21 and is best shown in FIGS. 1 and 5. This assembly has a socket portion 41 provided with a downwardly extended, unitary stud 42 which extends into the lower counter bore 26 and is there screw-threadably engaged by a nut and washer assembly 43. The upper counter bore 23 and the recess 24 conform to the mating surfaces of the socket portion. The joint assembly includes a ball portion 45 fitted in the socket portion for swivel movement relative thereto. The range of this swivel movement is limited in any suitable manner to approximately the range of movement of a natural ankle as is well-known in artificial ankle joints. The ball portion is provided with a unitary screw-threaded stud 46 extended upwardly from it. This stud adapts the foot for mounting in a conventional manner on the lower end of an artificial leg worn by the user of the foot. The rear keel, including the ball joint assembly, is thereby mounted on the leg in a position relative to the leg which corresponds to the position occupied by the ankle of a natural foot. The ball portion and socket portion are retained in engagement by a keeper 48 of any suitable construction.

The foot includes a toe member or forward keel 50, best shown in FIGS. 1, 2, 3, and 6, and constructed similarly to the rear keel 10. The forward keel is generally triangular as viewed transversely of the foot and has a planar, downwardly disposed sole surface 52. This surface is rectangular and is elongated along the foot, having a rearward end 53 and an opposite toe end 54. The forward keel has an upper surface 57 extending rearwardly and upwardly from the forward end to a point above the center of the sole surface and spaced therefrom a distance substantially equal to the spacing of the upper edge 32 from the sole surface 12 of the rear keel 10. The forward keel has a toe end 58 defined by a vertical planar surface which extends between the sole surface and the upper surface, giving the forward keel the general shape of the toe portion of a natural foot.

The forward keel 50 has a rearward side 60, best shown in FIGS. 1 and 6, which includes a planar peripheral surface 62 extending forwardly and upwardly from the rearward end 53 of the sole surface 52 to the upper surface 57. The peripheral surface is inclined to the sole surface of the forward keel at substantially the same angle as the peripheral surface 31 is inclined to the plane of the sole surface 12. This rearward side has a groove 64 centered transversely therein and having a width substantially equal to the width of the groove 33 in the rear keel 10. Centrally, the bottom of the groove in the forward keel is formed by a planar, upwardly and rearwardly facing wedging surface 65. This surface is inclined forwardly and upwardly from the sole surface of the forward keel at an angle substantially equal to the angle at which the wedging surface 35 of the rear keel is inclined to the corresponding sole surface.

The groove 64 has a lower portion 70 adjacent to the sole surface 52. This portion is substantially deeper and narrower than the central portion of the groove which provides the wedging surface 65. The lower portion of the groove is substantially equal in width to the slot 37, and the bottom surface of this lower portion is planar and parallel to the corresponding wedging surface. The upper portion 75 of this groove is the same width as its central portion which provides the wedging surface. The upper portion is substantially deeper than the central portion having a surface which extends forwardly from the wedging surface in a direction approximately parallel to the corresponding sole surface and then extends to the upper surface 57 in a direction approximately normal thereto. The groove thus provides a recess 77 at the intersection of the upper surface and the rearward side 60 of the forward keel 50.

When the foot is assembled, as shown in FIGS. 1, 2, and 3, the forward keel 10 is disposed with the rearward end 53 of its sole surface 52 juxtapositioned and substantially parallel to the forward end 14 of the sole surface 12 of the rearward keel 10 and with the wedging surfaces 35 and 65 facing each other in spaced relation. The keels are thus disposed with the forward keel extending forwardly from the rear keel.

The foot includes a unitary sheet member or hinge plate 80, shown in FIGS. 1, 2, and 7, which extends continuously beneath and is flatly engaged with the sole surfaces 12 and 52. This plate is a strip of resilient sheet material such as heat-treated steel. The plate is elongated longitudinally of the foot and has a rearward portion 82 flatly engaging the rearward keel, a forward portion 84 flatly engaging the forward keel, and a central portion 86 disposed beneath the respective juxtapositioned ends 14 and 53 of the sole surfaces. The rearward portion and the forward portion are individually rigidly connected to the corresponding keel by a plurality of screws 88 individually extended through bores 89 in the sole plate into screw-threaded engagement with the corresponding keel.

The central portion 86 of the hinge plate 80 is provided with a downwardly facing, concave groove 90 extended transversely across the plate. The depth of this groove is such as to give the hinge plate a desired degree of flexibility at its central portion so that the keels are connected by the plate for relative flexing movement in relation to each other. This flexing defines an axis, which extends transversely of the foot and is disposed adjacent to the groove, about which the keels pivot. The plate is adapted to assume a planar configuration when unrestrained and, therefore, resiliently urges the keels toward relative positions wherein the sole surfaces 12 and 52 lie in a common plane and the foot is in an unarched configuration 92, as shown in FIGS. 1 and 3, where the wedging surfaces 35 and 65 are relatively closely spaced. Pivotal movement of the keels into a position where the toe end 54 is disposed upwardly of this plane is prevented by engagement of the peripheral surfaces 31 and 62, respectively, of the forward side 30 of the rear keel and the rearward side 60 of the forward keel. However, the keels are free to pivot about the axis against the resilient urging of the sole plate in a direction such that the toe end 58 of the forward keel moves downwardly from this common plane and from the rear keel toward an arched configuration 93 of the foot, as shown in FIG. 1 in dash lines, in which the wedging surfaces are spaced relatively far apart.

The plate 80 is provided with a keyhole-shaped central opening 95. This opening has a larger, circular end portion 96 which is substantially equal in diameter to the lower counter bore 26 and is substantially coaxially aligned therewith. The opening has a narrower, rectangular slot portion 97 extending forwardly from the circular portion through the central portion 86 of the hinge plate and, therefore, adjacent to the axis about which the plate flexes.

The foot has a wedge assembly 100, shown in FIGS. 1, 2, 3, 8, and 9, disposed between the forward side 30 of the rear keel 10 and the rearward side 60 of the forward keel 50. The assembly is fixedly mounted on the hinge plate 80 and includes a cylindrically tubular collar 102. The exterior diameter of the collar is substantially greater than the width of the rectangular portion 97 of the opening 95 and is less than the diameter of its circular portion 96. The exterior diameter of the collar is such that it can be received within the slot 37 and the lower portion 70 of the groove 64 when the keels are in the unarched configuration 92. The collar is provided with a pair of diametrically opposite exterior grooves 104 which are dimensioned and proportioned slidably to receive the hinge plate 80 along the opposite sides of the slot portion 97 of the keyhole-shaped opening. These grooves are parallel and are obliquely related to the axis of the collar at an angle such that, when the plate is received in the grooves, the axis of the collar extends between the forward side of the rear keel and the rearward side of the front keel along a path of travel, indicated by the arrows 105, between these sides and their respective wedging surfaces 35 and 65. The collar has a downwardly disposed axial end 107 which is countersunk and an opposite axial end 108 which is planar and normal to the axis of the collar.

The wedge assembly 100 includes a screw 110 having a conical head 111, which is received in the countersunk end 107 of the collar 102, and a screw-threaded shank 112 which extends through the collar along the path 105 substantially into the recess 77. The shank does not screw-threadably engage the collar, but is rotationally fitted therein. The screw is provided with a relatively shallow bore 113 extended through it diametrically at a point spaced somewhat outwardly from the end 108 of the collar. A washer 115 is fitted coaxially over the shank between the collar and this bore and a pin 117 is fitted through the bore to retain the washer and the screw in the collar so that the screw is constrained from axial movement relatively to the plate and the wedging surfaces 35 and 65. The collar, washer, and pin thus mount the screw directly on the central portion 86 of the hinge plate 80 and indirectly on the keels 10 and 50 for rotational movement relative to the plate at a point adjacent to the axis about which the plate flexes.

The wedge assembly includes a wedge 120 disposed between the side 30 of the rear keel 10 and the side 60 of the forward keel 50 and oppositely received in the respective grooves 33 and 64 for opposite engagement by the wedging surfaces 35 and 65. The wedge has a central screw-threaded bore 122 which is screw-threadably engaged with the shank 112 of the screw 110. Opposite rotational movement of the screw thus moves the wedge along the path 105 toward and from the collar 102, the resilient hinge plate 80, and the axis about which the plate flexes.

The wedge 120 has an upper end 125 and lower end 126 which are rectangular, planar, and extend normal to the path 105. The wedge is disposed with its lower end facing the plate 80. The width of the upper end in a direction normal to the wedging surfaces 35 and 65 is substantially less than the corresponding width of the recess 77 and is substantially greater than the width of the lower end of the wedge, which has a width approximately equal to the diameter of the screw 110. The wedge has a pair of transversely opposite, planar sides 127 which are substantially parallel so that the lengths of the upper and lower ends of the wedge transversly of the foot are substantially equal. These sides are spaced a distance somewhat less than the transverse width of the grooves 33 and 64 and are slidably received in the grooves, as can be visualized from FIGS. 4, 6, and 8, so that the wedge is guided thereby along the path. The wedge has a pair of sides 128 and 129 which face, respectively, the wedging surface 35 of the rear keel 10 and the wedging surface 65 of the forward keel 50 and individually interconnect the transversely opposite sides of the wedge. The side of the wedge which faces the rear keel includes a upper planar portion 131 adjacent to the upper end of the wedge and extended parallel to the wedging surface of the rear keel. This side includes a lower planar portion 132 which is obliquely related to the path 105 and extends downwardly from the upper portion in convergent relation to the screw. The side of the wedge facing the forward keel is defined by a single planar surface which is obliquely related to the path and converges downwardly toward the screw from the upper end of the wedge.

Typically, the foot is provided, as is well known in the prosthetic art, with a layer 140 of flexible, resilient material such as rubber, which encloses the other elements of the foot except for the ball portion 45 and the upper end of the socket portion 41. Exteriorly, this layer has the shape of a natural foot. The portion of this layer beneath the hinge plate is provided with an opening 142 for access to the head 111 of the screw 110 and to the nut and washer assembly 43.

The foot is provided with a cap 150 of rigid material extending longitudinally of the foot above the rear keel 10 and mating upwardly with the portion of the resilient layer which is disposed upwardly of this keel. The underside of the cap conforms to the layer 140 and is engaged with it. The upper side of the cap has the shape of the portion of a natural foot which is above the ankle joint. The cap has a central bore 152 through which the stud 46 extends. This lower end of the bore is enlarged, forming a recess 154 dimensioned so that the cap does not engage the ball joint assembly and limit the swivel movement. The cap is upwardly engaged by a nut 156 which screw-threadably engages the stud and clamps the layer between the cap and the upper keel so that the resilience of the layer urges the foot to swivel at the ball joint assembly toward a position in which the studs 42 and 46 are aligned axially.

OPERATION

The operation of the described embodiment of the prosthetic foot of the present invention is believed to be clearly apparent and is briefly summarized at this point. Initially, the foot is mounted on an artificial leg by the stud 46. The foot is then adjusted for the height of the heel of the shoe which the user desires to wear on the foot.

If the shoe has substantially no heel, the foot is adjusted so that its elements are disposed in the unarched configuration 92, as shown in FIG. 1, by rotating the screw 110 so as to move the wedge 120 away from the plate 80. The screw is rotated by engaging its head 111 with an ordinary screwdriver or the like inserted through the opening 142. The screw is rotated until the wedge is positioned along the path 105 with its lower end 126 disposed at the bottom of the recess 77. With the wedge so positioned, each of its sides 128 and 129 are individually tightly engaged with the corresponding one of the wedging surfaces 35 and 65 since the hinge plate 80 urges the keels 10 and 50 into their unarched configuration in which the sole surfaces 12 and 52 lie substantially in the same plane.

If it is desired to wear the foot of the present invention with a shoe having a heel, indicated by numeral 160 in FIG. 1, of the greatest height for which the foot is adapted, the screw 110 is rotated so as to draw the wedge 120 toward the plate 80. As the wedge moves toward the plate, the sides 128 and 129 individually and firmly engage the corresponding wedging surfaces 35 and 65 and wedge these surfaces apart, pivoting the forward keel 50 about the flexural axis of the plate so that the toe end 58 of the forward keel pivots downwardly in relation to the rear keel, causing the foot to be "arched." As the wedge continues to move toward the plate, the "degree of arch," of course, increases. The foot is thus brought into the configuration 93 in which the sole surface 12 of the rear keel 10 is substantially horizontal and in which the toe end is disposed downwardly of this surface a distance equal to the height of the heel. This "arching" is analogous to the manner in which a natural foot adapts to a shoe heel of moderate height; that is, by pivoting the toes downwardly of the heel so that the heel is relatively horizontal and the tips of the toes are disposed downwardly of the heel.

The wedge 120 is positionable at any point along the path 105 by appropriate rotation of the screw 110 so that the foot is brought into the required degree of arch to adapt the foot to wear a shoe having a heel of any height within the range of adjustment of the foot. When the foot is at any degree of arch, an upward force on the toe portion 54 does not vary this degree of arch since the wedge blocks pivotal movement of the keels 10 and 50 in the direction which brings their respective wedging surfaces 35 and 65 together; that is, the direction in which the toe end 58 moves upwardly in relation to the sole surface 12. However, when the screw is rotated so as to move the wedge from the plate 80, the plate urges the forward keel to pivot upwardly in relation to the rear keel, decreasing the degree of arch. Conversely, opposite rotation of the screw moves the wedge toward the plate and pivots the forward keel downwardly against the resilient urging of the plate to increase the degree of arch of the foot. The wedge is thus adjustably positionable by the screw between the wedging surfaces selectively to arch and to flatten the keels in relation to each other.

The degree of arch of the prosthetic foot of the present invention is, therefore, selectively adjustable by rotation of the screw 110 so that the foot may be used with a shoe heel of any height within the range of adjustment provided by the foot. The degree of arch is readily adjusted by the user with an ordinary tool applied to the screw through the opening 142. The arched configuration produced by pivotal movement of the forward keel 50 in relation to the rear keel 10 in adjustment of the foot to shoe heels of different heights is similar to the configuration assumed by a natural foot when adapting to such heels. The foot can be mounted on a conventional artificial leg by the stud 42 and is adapted for use with advantageous prior art prosthetic foot structures such as a ball and socket joint assembly 40 and the layer 140 of resilient material.

Although the invention has been herein shown and described in what is conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. A prosthetic foot comprising:
   A. an ankle member adapted for mounting on a leg of a user and having a surface;
   B. a toe member extending forwardly from the ankle member and having a surface disposed in facing relation to said surface of the ankle member;
   C. means connecting said members for pivotal movement about an axis transversely of the foot so that the toe member pivots downwardly in relation to the ankle member to arch the foot and upwardly in relation to the ankle member to reduce such arch;
   D. a wedge disposed between and oppositely engaged by said surfaces; and
   E. means for moving the wedge between said surfaces toward the axis to increase the degree of arch and from the axis to decrease the degree of arch, thereby adjustably positioning said members to determine the degree to which the foot is arched.

2. The prosthetic foot of claim 1 wherein said positioning means comprises a screw-threaded member rotationally mounted in fixed axial position between the surfaces adjacent to said axis and screw-threadably engaged with the wedge so that opposite rotation of the screw-threaded member moves the wedge toward and from the axis.

3. A prosthetic foot comprising:
   A. an ankle member adapted to be mounted on a leg of a user;
   B. a toe member;
   C. means interconnecting the ankle member and the toe member for relative flexing movement with said members in spaced relation and providing facing surfaces;

D. a wedge disposed between said surfaces; and

E. means for adjustably positioning the wedge between said surfaces selectively to arch and to flatten the interconnected ankle and toe members.

4. A prosthetic foot comprising:

A. an ankle member adapted to be mounted on a leg of a user of the foot in a position corresponding to the position of the ankle joint of a natural foot, said member having a forward end, a downwardly disposed sole surface, and a forwardly disposed wedging surface extending forwardly and upwardly from the sole surface;

B. a toe member forwardly spaced from the ankle member and having a downwardly disposed sole surface, a rearwardly disposed wedging surface extending forwardly and upwardly from the sole surface in spaced facing relation to the wedging surface of the ankle member, and a toe end;

C. a continuous resiliently flexible sheet member extended beneath the sole surfaces of the ankle member and the toe member having a rearward portion rigidly connected to the ankle member, a forward portion rigidly connected to the toe member, and a central portion disposed between the ankle member and the toe member which flexes so that the ankle member and the toe member move pivotally in relation to each other about an axis extended transversely of the foot, the sheet member being adapted to urge the ankle member and the toe member into a relative position wherein their respective sole surfaces lie substantially in a common plane;

D. a wedge disposed between the wedging surfaces and oppositely engaged thereby; and E. means for moving the wedge between the wedging surfaces toward and from the sheet member, movement of the wedge toward the sheet member wedging said surfaces apart and pivoting the toe member downwardly in relation to the ankle member to arch the sheet member, the sheet member urging the toe member upwardly in relation to the ankle member to decrease the arch as the wedge moves from the sheet member.

5. The prosthetic foot of claim 4 wherein each wedging surface has a groove extended along the path of the wedge, the wedge being received in the groove for guidance thereby along said path.

6. The prosthetic foot of claim 4 wherein the means for moving the wedge comprises a screw-threaded member rotationally mounted in fixed axial positions between the surfaces and screw-threadably connected to the wedge so that rotation of the screw-threaded member moves the wedge toward and from the sheet member.

7. The prosthetic foot of claim 6 wherein the screw-threaded member is mounted on the central portion of the sheet member for rotational movement relative thereto while being constrained from movement axially in relation thereto and is screw-threadably engaged with the wedge.

* * * * *